United States Patent [19]

Mazarguil et al.

[11] 4,034,139

[45] July 5, 1977

[54] GRAFTED MINERAL CARRIERS FOR FIXING ENZYMES

[75] Inventors: Honore Mazarguil, Ramonville-St Agne; François Meiller, Palaiseau; Pierre Monsan, Toulouse, all of France

[73] Assignee: Rhone-Poulenc Industries, Paris, France

[22] Filed: Apr. 16, 1975

[21] Appl. No.: 568,796

[30] Foreign Application Priority Data

Apr. 19, 1974 France .............................. 74.13687

[52] U.S. Cl. .............................. 428/405; 428/406; 428/429; 427/219; 427/220; 427/221; 427/399; 195/63; 195/68; 260/825; 260/824 R; 210/31 C; 55/67; 252/430; 252/431 R

[51] Int. Cl.² .................. B32B 27/14; B01J 21/00

[58] Field of Search .......... 428/405, 391, 429, 406; 427/219, 220, 221, 399; 195/63, 68; 260/825, 824 R; 210/31 C; 55/67; 252/430, 431 R

[56] References Cited

UNITED STATES PATENTS

| | | | |
|---|---|---|---|
| 3,560,254 | 2/1971 | Seddon | 427/399 X |
| 3,830,738 | 8/1974 | Cottrell | 428/405 X |

*Primary Examiner*—Ralph S. Kendall
*Attorney, Agent, or Firm*—McDougall, Hersh & Scott

[57] ABSTRACT

The invention concerns grafted mineral carriers comprising oxides, hydroxides and other insoluble, porous mineral compounds, upon which are grafted haloalkylsilane groups which may or may not be substituted and whose alkyl residue comprises from 3 to 11 carbon atoms. They are used as industrial catalyst carriers, in chromatography and more particularly for fixing enzymes.

8 Claims, No Drawings

GRAFTED MINERAL CARRIERS FOR FIXING ENZYMES

This invention concerns grafted mineral carriers and a process for the preparation of said carriers and the use thereof for fixing enzymes.

Mineral carriers are known products but, for some uses, as for example fixing enzymes, it is necessary to modify the chemical nature of the mineral carrier by grating thereon a group which improves the fixing as between the carrier and the enzyme. Thus, it has been proposed that silanes should be grafted onto the mineral carriers, which permit a certain number of direct fixing reactions to be carried out as between the carriers and certain enzymes.

In other cases of connecting a grafted carrier and an enzyme, it is often necessary, if the fixing is to be stable in respect of time, to use intermediate compounds such as dicyclohexylcarbodiimide, thiophosgene or glutaraldehyde.

In addition, iodine-containing polymer carriers have also been proposed, but these suffer from the disadvantage of being sensitive to solvents, temperature and pressure, and this limits the uses to which they can be put. Moreover, they suffer from the disadvantage of having a large amount of iodine-containing groups which run the risk of having an effect on the activity of the enzyme which is subsequently fixed on the carrier.

The carriers of the invention, which can be used in many areas, are insensitive to solvents, temperature and pressure and make it possible for fixing enzymes not only to carry out new reactions, avoid using intermediate compounds, and avoid the presence of an excessively large number of active loci, but also make it possible, in a simple manner and with excellent yields, to effect stable enzyme fixings which are resistant to denaturation factors.

The grafted carriers of this invention comprise oxides, hydroxides or other porous, insoluble mineral compounds, and are characterized in that they carry substituted or unsubstituted haloalkylsilane groups whose alkyl residue comprises from 3 to 11 carbon atoms.

These grafted carriers are produced by reacting a mineral carrier having hydroxyl groups with a haloalkylsilane having from 1 to 3 groups which are reactive with the hydroxyl groups of the carrier.

The mineral carrier used must have hydroxyl groups, a grain size range of from 40 $\mu$ to 5 mm, a specific surface area of the order of from 2 to 600 sq. m/g and preferably from 20 to 70 sq. m/g, when it is intended for fixing enzymes, a pore diameter of the order of from 50 to 10,000 A and a pore volume of from 0.5 to 1.8 ml/g.

The following are illustrative of carriers which have these characteristics: aluminas, brick, glass, mineral silicates, metal oxides and more particularly silicas.

The compound to be grafted is a haloalkylsilane having the following general formula:

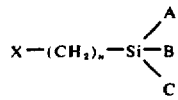

in which:

X represents a halogen atom: chlorine, bromine or iodine;

$n$ is an integer of from 3 to 11;

A, B and C, which are similar to or different from each other, represent a Cl atom, or a methoxy, ethoxy, methyl or ethyl group, with the condition that at least one of the substituents A, B or C is capable of reacting with an OH group of the mineral carrier.

The following can be mentioned as compounds which are particularly suited for grafting: triethoxy-bromopropylsilane, trimethoxy-iodopropylsilane, triethoxy-iodopropylsilane, triethoxy-chlorobutylsilane, trichloro-chloropropylsilane, dimethylchlorochloropropylsilane, methyldichloro-iodoundecylsilane.

The grafting reaction can be carried out by any known processes in a solvent or aqueous medium, at atmospheric pressure or under pressure, and generally at elevated temperature.

The grafted carriers of this invention can be used as industrial catalyst carriers, in chromatography, affinity chromatography, and more particularly for fixing enzymes.

In the latter case, a very large number of enxymes can be fixed, represented in particular by:
oxidoreductases, such as glucose oxidase;
hydrolases, such as lipase, pectinase, trypsine, urease, glucoamylase and α-amino-acylase.

Fixing of the enzyme is effected in accordance with any known processes, either cold in an aqueous solution which is buffered in accordance with the pH value compatible with the enzyme, or hot in hydrocarbons or chlorinated solvents, in accordance with the process of U.S. Patent application Ser. No. 494,818, filed Aug. 5, 1974 now abandoned. The particular process will depend on the nature of the enzyme. Likewise, the choice of the carrier and the halogenated graft depends on the specificity and the actual reaction characteristics of the enzyme.

The enzymes, which are fixed in this way, are particularly stable and resistant to denaturation factors, pH and temperature.

Embodiments of the invention are given hereinafter by way of illustration and not limitation.

EXAMPLE 1

100 g of a silica, in the form of microballs, characterized by a grain size of from 100 to 200 $\mu$, a specific surface area of 44 sq. m/g, a pore diameter of 660 A and a pore volume of 0.9 ml/g, is dired at 150° C under vacuum for a period of 4 hours.

The dried silica is introduced into 200 ml of a solution of 20 g of triethoxy-bromopropylsilane in xylene, and the mixture is heated for 8 hours at 140° C. After cooling, the grafted silica is drained, washed with acetone and dried under vacuum. The product contains 0.4% by weight of bromine.

EXAMPLE 2

Operation is as in Example 1, but with 20 g of trimethoxy-iodopropylsilane dissolved in 200 ml of xylene at boiling temperature.

The grafted product contains 0.45% by weight of iodine.

EXAMPLE 3

100 g of a silica having a grain size of from 200 to 400 $\mu$, a specific surface area of 50 sq. m/g, a pore diameter of 600 A and pore volume of 1.1 ml/g, is dried under vacuum at 150° C for 4 hours.

The dried silica and 250 ml of toluene containing 10 g of triethoxy-chlorobutylsilane are introduced into an autoclave, and the mixture is heated for 2 hours at 190° C under autogenous pressure (5 bars).

After cooling, the grafted silica is drained, rinsed with toluene, and then with acetone, and finally dried. The product contains 0.7% by weight of chlorine.

EXAMPLE 4

A hydrogel is prepared by stirring, in a 2 liter beaker, 230 ml of a 120 g/l $H_2SO_4$ aqueous solution to which a solution of sodium silicate (containing 220 g/l of $SiO_2$) is added dropwise. When the pH value is 3.8, the sol produced, together with 2 drops of sodiumalkylsulfonate, is poured into a balloon flask containing 8 l of trichloroethylene, and the mixture is stirred vigorously. In a few minutes hydrogel balls are formed. 1 liter of ammoniated water, pH 9, is then added, followed by a filtration step.

The balls are washed 3 times with N/10 HCl, then with water. The resulting hydrogel contains 80% of water and the size of the balls is less than 200μ.

120 g of hydrogel, 15 g of triethoxy-iodopropylsilane and 200 ml of benzene are introduced into a balloon flask. The mixture is heated at 80° C and 95 ml of water is recovered by azeotropic distillation.

After cooling, the grafted product is drained, washed with acetone and dried.

The specific surface area of the resulting product is 425 sq. m/g, and its pore volume is 1.1 ml/g.

The iodine content is 2.1% by weight.

EXAMPLE 5

Fixing glucoamylase in aqueous medium:

Fixing is effected on the grafted silica of Example 1 (Text A) and on the grafted silica of Example 2 (Test B).

1 g of carrier is added to 20 ml of a 0.1 M acetate buffer, pH 4.5, solution, containing 20 mg of glucoamylase, and the resulting dispersion is stirred for 18 hours at 4° C.

After decantation, the carriers are washed 3 times with distilled water, and their activity is measured.

The carrier-enzyme complexes produced are introduced into 10 ml of a 3% by weight starch solution in a 0.1 M acetate buffer, pH 4.5, and left in contact with stirring for 10 minutes at 40° C.

After separation, a measurement of the reducing sugars liberated is carried out on the liquid phase, by colorimetry with 3,5-dinitrosalicyclic acid. Several washing operations and activity measuring operations are thus carried out in succession. Between each measurement operation, the complexes are preserved in 2 M NaCl solution.

The results related to the glucose and expressed in μ mol of glucose liberated/min/g of carrier are as follows:

| | | Test A | Test B |
|---|---|---|---|
| activity | initial: | 8.5 | 1.4 |
| | after 5 days: | 5 | 1 |
| | after 10 days: | 0 | 0.7 |

EXAMPLE 6

Fixing glucoamylase in organic medium:

Operation is as in Example 5, except that 1 g of carrier is added to 30 ml of a dispersion of anhydrous chloroform containing 50 mg of glucoamylase. The mixture which is agitated by sonic vibration is heated under reflux for 2 hours. The solvent is then removed under vacuum.

The carriers are washed with distilled water and then with NaCl, and their activity is measured. The following results are obtained:

| | | Test A | Test B |
|---|---|---|---|
| activity | initial: | 15.6 | 1.2 |
| | after 5 days: | 11 | 0.7 |
| | after 10 days: | 4.5 | 0 |

It is found that the silica carrying a bromine-containing graft fixes more enzyme than the silica with an iodine-containing graft.

EXAMPLE 7

Fixing glucose oxidase in aqueous medium:

The enzyme is fixed as described in Example 5.

The enzymatic activity is determined as follows: 1 g of carrier-enzyme complex, 20 ml of a solution containing 18 g/l of glucose in a 0.1 M, pH 5.6, acetate buffer, containing 100 mg/l of O-dianisidine, and 40 ml of a solution containing 2 mg/l of peroxidase in a 0.1 M acetate buffer, pH 5.6, are mixed. The variation in absorbance at 460 nm is followed in dependence on time.

The results expressed in μ mol of $H_2O_2$ liberated/min/g of carrier are as follows:

| Test A: | Initial activity | 3.8 |
|---|---|---|
| | Activity after 1 month | 1.76 |
| Test B: | Initial activity | 4 |
| | Activity after 1 month | 1.88 |

It can be deduced from the above that fixing the enzyme in aqueous medium gives results which are very close, whether the carrier has a bromine-containing or an iodine-containing graft.

EXAMPLE 8

Fixing glucose oxidase in organic medium:

The enzyme is fixed as in Example 6, and the enzymatic activity is determined as in Example 7. The following results are obtained:

| Test A: | Initial activity | 2.60 |
|---|---|---|
| | Activity after 1 month | 0.80 |
| Test B: | Initial activity | 5.20 |
| | Activity after 1 month | 5.20 |

Fixing of the enzyme on a carrier with an iodine-containing graft is better than that produced on a carrier with a bromine-containing graft. In addition, the iodine-containing carrier-enzyme complex is more stable in respect of time.

EXAMPLE 9

Fixing pectinase in aqueous medium:

As in the preceding examples, the enzyme is fixed on the grafted silica of Example 1 (Test A) and on the grafted silica of Example 2 (Test B).

2 g of grafted silica is added to 8 mg of pectinase in solution in 20 ml of water, then the mixture is agitated at 4° C for 24 hours.

After decantation, the carrier-enzyme complex is washed 3 times with 20 ml of distilled water, 3 times with 20 ml of M NaCl, and finally 3 times with 20 ml of 0.1 M acetate buffer, pH 4.

Enzymatic activity is then measured as follows:

2 g of the carrier-enzyme complexes are dispersed in 10 ml of a 1% solution of polygalacturonic acid in 0.01 M acetate buffer, pH 4, and then the dispersion is heated for 10 minutes at 35° C.

In 5 ml of the medium, the polygalacturonic acid which has not been converted is defecated by the addition of 0.3 ml of a 9% zinc sulfate aqueous solution and 0.3 ml of 0.5 N sodium hydroxide. After centrifuging, the D galacturonic acid present in the part which floats on the surface is determined by the method using dinitrosalicylate.

This measurement of enzymatic activity is repeated after 2, 3 and 5 days. After each measuring operation, the carrier-enzyme complexes are washed by being brought into contact with 20 ml of 2 M NaCl for 15 hours, then rinsed with distilled water, and then with the acetate buffer.

The following results are obtained, expressed in the form of $\mu$ mol of galacturonic acid hydrolyzed/min/g of carrier:

| | | Test A | Test B |
|---|---|---|---|
| activity | initial | 13.30 | 11.80 |
| | after 2 days | 13.30 | 10.85 |
| | after 3 days | 13.30 | 8.20 |
| | after 5 days | 12.70 | 7.50 |

It is found that the carrier with a bromine-containing graft fixes more enzyme than the carrier with an iodine-containing graft. Moreover, the bromine-containing graft carrier gives a complex which is more stable in respect of time.

The action of the bromine-containing graft carrier-pectinase complex is then tested continuously: 6 g of the complex is placed in a column which is 20 cm in height and 1 cm in diameter. The column, which is thermostatically controlled to a temperature of 25° C, is fed with a solution of 0.4% polygalacturonic acid in 0.01 M acetate buffer, pH 4, at a rate of 52 ml/h.

The column operated without loss of activity for a period of 10 days, giving a hydrolysis rate of 42%. This shows the high level of stability of the complex.

EXAMPLE 10

Fixing pectinase in organic medium on the grafted silicas of Examples 1 and 2:

500 mg of commercial pectinase, then 2 g of the grafted carrier, are dispersed by sonic vibration in 50 ml of anhydrous benzene. The dispersion is then heated to boiling temperature, and maintained at that temperature for 1 hour.

The solvent is evaporated under reduced pressure and the carrier-enzyme complex produced is washed 3 times with 20 ml of distilled water, then 3 times with 20 ml of M NaCl, and finally, 3 times with 20 ml of 0.1 M acetate buffer, pH 4.

Enzymatic activity is measured in the same manner as in Example 9. The following results are obtained:

| Test A: | initial activity | 10.15 |
|---|---|---|
| | activity after 2 days | 10.15 |
| Test B: | initial activity | 4.70 |
| | activity after 2 days | 3.80 |

As in Example 9, it is found that the carrier with the bromine-containing graft fixes more enzyme than the carrier with the iodine-containing graft.

EXAMPLE 11

Fixing $\alpha$-aminoacylase in aqueous medium:

As in the preceding examples, the grafted silicas of Examples 1 and 2 are used.

10 ml of 0.1 M phosphate buffer, pH 7, containing 10 mg of enzyme and 1 g of carrier are brought into contact with agitation at 4° C, for a period of 48 hours.

After separation, the carrier-enzyme complex is washed 3 times with 10 ml of distilled water and 10 times with 10 ml of M NaCl.

Enzymatic activity is measured. 1 g of the carrier-enzyme complex and 10 ml of 0.1 M solution of acetyl DL-methionine in 0.1M phosphate buffer, pH 7, are heated at 40° C for 30 minutes. The L-methionine liberated is determined by the method using ninhydrine.

The results obtained, expressed in the form of $\mu$ mol of L-methionine liberated/l/g of carrier are as follows:

Silica with bromine-containing graft — Activity: 100
Silica with iodine-containing graft — Activity: 30

EXAMPLE 12

Fixing trypsine:

This fixing operation is carried out on the grafted silicas of Examples 1 (Test A) and 2 (Test B).

2 g of carrier is added to 2 mg of trypsine dispersed by sonic vibration in 20 ml of hexane, then the mixture is raised to boiling temperature and maintained at that temperature for 1 hour.

The hexane is then evaporated and the carrier-enzyme complexes are washed 3 times with 20 ml of distilled water, then 3 times with 20 ml of 1 M NaCl.

1 ml of water and then 9 ml of a solution of 0.3% by weight caseine, in 0.025 M phosphate-citrate buffer, pH 7, are added to the complexes produced above. The dispersions are then heated at 37° C for 10 minutes. After cooling and decantation, 4 ml of the solutions are taken off and 4 ml of a 10% by weight aqueous solution of trichloroacetic acid is added to each solution; the excess caseine precipitates and is filtered, then the content of peptides is measured on the filtrate, using the Lowry method.

The carrier-enzyme complexes are again washed with M NaCl, and a fresh measurement of enzymatic activity is carried out after 1 week.

The results expressed in $\mu$g of peptides liberated/ml/min/g of carrier are as follows:

| Test A: | initial activity | 34.5 |
|---|---|---|
| | activity after 1 week | 20.5 |
| Test B: | initial activity | 4.5 |
| | activity after 1 week | 4.5 |

It is found that the silica with the bromine-containing graft fixes more enzyme than the silica with the iodine-containing graft, but that on the other hand the latter gives a complex which is more stable in respect of time.

EXAMPLE 13

Fixing urease:

1 g of urease and 6 g of the grafted silica of Example 2 are dispersed in 150 ml of chloroform. The resulting dispersion is then heated under the reflux for 1 hour. The chloroform is then evaporated and the carrier-enzyme complex is washed 3 times with 20 ml of 0.1 M phosphate buffer, pH 7, and then 3 times with 20 ml of 2M NaCl.

0.5 g of the resulting complex is suspended in 5 ml of 0.025 M phosphate buffer, pH 7, and left in contact for 2 minutes. 2 ml of a 20 g/l aqueous solution of urea is then added, and left in contact for 2 minutes. The reaction is stopped by filtration. 5 ml of N/10 HCl is added to the filtrate and the excess HCl is determined by means of 0.05 N NaOH.

The washing and activity measuring operations are repeated several times. The results expressed in $\mu$ mol of $NH_3$ produced in 2 minutes are summarized in the following table.

TABLE

| Conditions of preservation | | Dry in a cooler at 4° C | In suspension in phosphate buffer in a cooler |
|---|---|---|---|
| Activity | initial | 200 | 200 |
| | after 4 days | 266 | 278 |
| | after 11 days | 218 | 283 |
| | after 19 days | 168 | 268 |
| | after 27 days | 187 | 228 |

Examination of this table leads one to conclude that activity is virtually constant in respect of time, irrespective of the conditions of preservation.

EXAMPLE 14

Fixing lipase:

Fixing is carried out in aqueous medium on the grafted silicas of Examples 1 (Test A), 2 (Test B) and 3 (Test C).

20 ml of a 1% lipase solution in distilled water and 2 g of carrier are introduced into test tubes. The test tubes are then subjected to slow and regular agitation for 24 hours at 40° C.

The resulting carrier-enzyme complexes are separated from the lipase solution by decantation, and washed 3 times with 20 ml of distilled water. They are then suspended in 25 ml of a 2% solution of biliary salts in distilled water for 3 hours at 4° C, with slow agitation, in order to desorb the enzyme which is weakly linked to the carrier. The complexes are then washed with distilled water.

Enzymatic activity is then measured by the Desnuelle method, applied to an emulsion of olive oil. The fatty acids liberated are measured by potentiometry at a contant pH value.

Enzymatic activity expressed in regard to the amount of fatty acids liberated in $\mu$ equivalent of carrier is 8 for Test A, 6 for Test B and 14 for Test C.

The complex produced by fixing the lipase on the silica with a chlorine-containing graft therefore has the greatest activity.

We claim:

1. Grafted mineral carriers comprising oxides, hydroxides or other porous, insoluble mineral compounds having a grain size range of from 40 $\mu$ to 5 mm, a specific surface area of from 2 to 600 sq. m/g, a pore diameter of from 50 to 10,000 A and a pore volume of from 0.5 to 1.8 ml/g in which a mineral carrier having hydroxyl groups is grafted with a substituted or unsubstituted haloalkylsilane having the general formula

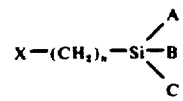

in which:

X represents a chlorine, bromine or iodine atom;

n is an integer of from 3 to 11;

A, B and C, which are the same or different, are selected from the group consisting of a chlorine atom, a methoxy, ethoxy, methyl or ethyl group, in which at least one of the substituents A, B or C is reacted with an OH group of the carrier.

2. A process for the preparation of the carriers according to claim 1, characterized in that a mineral carrier having hydroxyl groups is reacted with a haloalkylsilane having 1 to 3 groups which are reactive with the hydroxyl groups of the carrier.

3. A process according to claim 2, characterized in that the mineral carrier has hydroxyl groups.

4. A process according to claim 2, characterized in that the carrier is selected from the group consisting of silicates, metal oxides and silicas.

5. A process according to claim 2, characterized in that the haloalkylsilane is selected from the group consisting of triethoxy-bromopropylsilane, trimethoxy-iodopropylsilane, triethoxy-iodopropylsilane, triethoxy-chlorobutylsilane, trichloro-chloropropylsilane, dimethylchloro-chloropropylsilane, methyldichloro-iodoundecylsilane.

6. A process as claimed in claim 2 in which the carrier is an alumina.

7. A process as claimed in claim 2 in which the carrier is brick.

8. A process as claimed in claim 2 in which the carrier is glass.

* * * * *